United States Patent
Klaus-Nietrost et al.

(10) Patent No.: US 11,321,658 B2
(45) Date of Patent: May 3, 2022

(54) ENCODING A CELLULOSE PRODUCT

(71) Applicant: LENZING AKTIENGESELLSCHAFT, Lenzing (AT)

(72) Inventors: Christoph Klaus-Nietrost, Vöcklabruck (AT); Richard Herchl, Ried im Innkreis (AT); Christian Weilach, Vöcklabruck (AT)

(73) Assignee: LENZING AKTIENGESELLSCHAFT

( * ) Notice: Subject to any disclaimer, the term of this patent is extended or adjusted under 35 U.S.C. 154(b) by 23 days.

(21) Appl. No.: 16/962,503

(22) PCT Filed: Jan. 14, 2019

(86) PCT No.: PCT/EP2019/050750
§ 371 (c)(1),
(2) Date: Jul. 15, 2020

(87) PCT Pub. No.: WO2019/138096
PCT Pub. Date: Jul. 18, 2019

(65) Prior Publication Data
US 2020/0349491 A1    Nov. 5, 2020

(30) Foreign Application Priority Data

Jan. 15, 2018 (EP) .................... 18151679

(51) Int. Cl.
*G06Q 10/06* (2012.01)
*G06F 16/22* (2019.01)
(Continued)

(52) U.S. Cl.
CPC ......... *G06Q 10/06395* (2013.01); *D01F 2/00* (2013.01); *D01F 2/06* (2013.01);
(Continued)

(58) Field of Classification Search
CPC ........... G06Q 10/00–50/00; D01F 1/00–13/00; G01N 1/00–37/00
(Continued)

(56) References Cited

U.S. PATENT DOCUMENTS 3,801,273 A    4/1974 Mays
3,937,671 A    2/1976 Gruntfest et al.
(Continued)

FOREIGN PATENT DOCUMENTS

DE    44 09 335 A1    9/1994
DE    198 82 319 T1    7/2000
(Continued)

OTHER PUBLICATIONS

International Search Report of corresponding PCT/EP2019/050750, dated Feb. 12, 2019, 6 pages.
(Continued)

*Primary Examiner* — Alan S Miller
(74) *Attorney, Agent, or Firm* — Lewis Roca Rothgerber Christie LLP (57) ABSTRACT

Method of identifying a product which comprises cellulose, wherein in the method a data set is determined which is indicative for multiple constituents of the product or a preform of the product, and the data set which is correlated with the product or the preform is stored in a database.

15 Claims, 3 Drawing Sheets

(51) Int. Cl.
  *D01F 2/00* (2006.01)
  *D01F 2/06* (2006.01)
  *G01N 33/36* (2006.01)
  *G06Q 10/08* (2012.01)
  *G06Q 10/00* (2012.01)
  *G06Q 50/04* (2012.01)

(52) U.S. Cl.
  CPC ............ *G01N 33/36* (2013.01); *G06F 16/22* (2019.01); *G06Q 10/087* (2013.01); *G06Q 10/30* (2013.01); *G06Q 50/04* (2013.01)

(58) Field of Classification Search
  USPC .............................................. 705/7.11–7.42
  See application file for complete search history.

(56) References Cited

U.S. PATENT DOCUMENTS

| | | | |
|---|---|---|---|
| 4,246,221 A | 1/1981 | McCorsley | |
| 4,345,039 A | 8/1982 | Cowan et al. | |
| 5,240,530 A | 8/1993 | Fink | |
| 5,598,980 A | 2/1997 | Dilly-Louis et al. | |
| 5,601,767 A | 2/1997 | Firgo et al. | |
| 5,675,784 A * | 10/1997 | Maxwell | G06Q 10/10 |
| 5,722,603 A | 3/1998 | Costello et al. | |
| 5,761,093 A * | 6/1998 | Urbish | G05B 19/41875 |
| | | | 700/110 |
| 5,942,444 A * | 8/1999 | Rittenburg | C12Q 1/6813 |
| | | | 435/7.1 |
| 6,258,304 B1 | 7/2001 | Bahia | |
| 7,996,172 B2 * | 8/2011 | Bauer | G16H 10/40 |
| | | | 702/85 |
| 10,360,238 B1 * | 7/2019 | O'Brien | G06F 16/25 |
| 2001/0025282 A1 * | 9/2001 | Ohishi | G06Q 10/06 |
| 2002/0161906 A1 * | 10/2002 | Teraura | G06Q 10/087 |
| | | | 709/230 |
| 2003/0150909 A1 * | 8/2003 | Markham | G06Q 50/00 |
| | | | 235/376 |
| 2003/0158795 A1 * | 8/2003 | Markham | G06Q 10/087 |
| | | | 705/28 |
| 2004/0030426 A1 * | 2/2004 | Popp | G05B 19/41865 |
| | | | 700/97 |
| 2004/0030435 A1 * | 2/2004 | Popp | G06Q 50/06 |
| | | | 700/110 |
| 2004/0054516 A1 * | 3/2004 | Oyasato | G06Q 10/10 |
| | | | 703/22 |
| 2005/0004682 A1 * | 1/2005 | Gaddis | G06Q 10/06 |
| | | | 705/1.1 |
| 2005/0112610 A1 * | 5/2005 | Lee | C12Q 1/6876 |
| | | | 435/6.15 |
| 2006/0054682 A1 * | 3/2006 | de la Huerga | G16H 20/10 |
| | | | 235/375 |
| 2007/0016322 A1 * | 1/2007 | Kataoka | G05B 19/4183 |
| | | | 700/226 |
| 2007/0055638 A1 * | 3/2007 | Kaup | G06Q 30/0283 |
| | | | 705/400 |
| 2008/0061124 A1 * | 3/2008 | Langlois | G06Q 30/06 |
| | | | 340/572.1 |
| 2008/0154749 A1 * | 6/2008 | D'hooghe | G06Q 50/26 |
| | | | 705/28 |
| 2008/0216255 A1 * | 9/2008 | Poovey | D06H 1/04 |
| | | | 442/187 |
| 2009/0070273 A1 * | 3/2009 | Moryto | G06Q 40/12 |
| | | | 705/37 |
| 2011/0037764 A1 * | 2/2011 | Saleem | G01S 5/0027 |
| | | | 345/419 |
| 2011/0146930 A1 * | 6/2011 | Kane | C09K 11/7766 |
| | | | 252/301.4 R |
| 2012/0084220 A1 * | 4/2012 | Rider | G06Q 30/018 |
| | | | 705/317 |
| 2012/0095930 A1 * | 4/2012 | Rider | G06Q 30/018 |
| | | | 705/317 |
| 2012/0150733 A1 * | 6/2012 | Belady | G06Q 20/10 |
| | | | 705/317 |
| 2012/0209783 A1 * | 8/2012 | Smith, Jr. | G06Q 20/384 |
| | | | 705/308 |
| 2013/0054382 A1 * | 2/2013 | Holman | G07F 17/0078 |
| | | | 705/15 |
| 2015/0329771 A1 | 11/2015 | Danielec et al. | |
| 2016/0283917 A1 | 9/2016 | Nunn et al. | |
| 2017/0011362 A1 * | 1/2017 | Whitman | G06K 7/10316 |
| 2017/0262860 A1 * | 9/2017 | Teplinsky | G06Q 30/0185 |
| 2017/0292206 A1 | 10/2017 | Jung et al. | |
| 2018/0100810 A1 * | 4/2018 | Sahu | G01N 21/94 |
| 2018/0114168 A1 * | 4/2018 | Ryan | G06Q 10/08 |
| 2018/0276679 A1 * | 9/2018 | Fang | G06Q 10/08 |
| 2018/0330241 A1 * | 11/2018 | Seaton | G06Q 10/06 |

FOREIGN PATENT DOCUMENTS

| | | |
|---|---|---|
| DE | 696 18 988 T2 | 9/2002 |
| EP | 0 205 346 B1 | 12/1986 |
| EP | 0 636 646 A1 | 2/1995 |
| EP | 0 681 896 A1 | 11/1995 |
| EP | 3 339 504 A1 | 6/2018 |
| EP | 3 511 140 A1 | 7/2019 |
| WO | WO 96/07778 A1 | 3/1996 |
| WO | WO 97/021490 A2 | 6/1997 |
| WO | WO 02/40766 A2 | 5/2002 |
| WO | WO 2013/182801 A1 | 12/2013 |
| WO | WO 2014/045062 A1 | 3/2014 |
| WO | WO 2014/086579 A1 | 6/2014 |
| WO | WO 2016/123643 A1 | 8/2016 |
| WO | WO 2017/019802 A1 | 2/2017 |
| WO | WO-2017019802 A1 * | 2/2017 ............ C08B 16/00 |

OTHER PUBLICATIONS

Search Report of corresponding EP 18151679.0, dated Jul. 11, 2018, 10 pages.
Office Action of corresponding EP 18151679.0, dated Jun. 24, 2020, 9 pages.
Office Action of corresponding TW application 108101354, dated Feb. 18, 2020, 24 pages with English translation.
Ouchi, et al., "A new methodology to recycle polyester from fabric blends with cellulose," Cellulose 17.1 (2010), pp. 215-222.
Golova, et al., "Structure—Properties Interrelationships in Multicomponent Solutions Based on Cellulose and Fibers Spun Therefrom," Cellulose—Fundamental Aspects, chapter 13, 2013, pp. 303-342.
Scholz, "Thermoplastisches Polyurethan," Index I FAPU 15, Nov./Dez. 2002 I Fachartikel, 4 pages.
Tausif, et al., "Mechanical Properties of Nonwoven Reinforced Thermoplastic Polyurethane Composites," Materials 2017, 10, 618, 13 pages.
"Einzigartig wie ein Fingerabdruck", Markt & Technik 38/2013, 2 pages.
Zamani, et al., "Carbon Footprint of Textile Recycling: A Case Study in Sweden," Journal of Industrial Ecology, Aug. 1, 2015, pp. 676-687, XP055484757.
Comnea-Stancu, et al., "On the Identification of Rayon/Viscose as a Major Fraction of Microplastics in the Marine Environment: Discrimination between Natural and Manmade Cellulosic Fibers Using Fourier Transform Infrared Spectroscopy," Applied Spectroscopy, vol. 71, No. 5, Sep. 20, 2016, pp. 939-950, XP55489628.

* cited by examiner

ENCODING A CELLULOSE PRODUCT

CROSS-REFERENCE TO RELATED APPLICATION

This application is a National Phase Patent Application and claims priority to and the benefit of International Patent Application No. PCT/EP2019/050750, filed Jan. 14, 2019, which claims priority to and the benefit of European Patent Application No. EP 18151679.0, filed Jan. 15, 2018, the entire contents of all of which are incorporated herein by reference.

FIELD OF INVENTION

The invention relates to a method of identifying a product which comprises cellulose and to a use.

BACKGROUND

As viscose fibers, chemical fibers and regenerated fibers are denoted, which are manufactured by means of a wet spinning method which is called viscose-method. The starting raw material of the viscose-method is cellulose which is provided on the basis of wood. From this starting raw material wood, the highly pure cellulose in form of chemical pulp is obtained. In subsequent process stages, the pulp is first treated with caustic soda, whereby alkali cellulose is formed. In a subsequent conversion of said alkali cellulose with carbon disulfide, cellulose-xanthogenate is formed. From this, by further supplying caustic soda, the viscose-spinning solution is generated which is pumped through holes of shower-like spinning nozzles into a spinning bath. There, one viscose-filament per spinning nozzle hole is generated by coagulation. The such manufactured viscose-filaments are subsequently cut to viscose-staple fibers.

Lyocell denotes a regenerated fiber type comprising cellulose, which is manufactured according to a direct solvent method. The cellulose for the lyocell-method is extracted from the raw material wood. The such obtained pulp may subsequently be solved in N-methylmorpholine-N-oxide (NMMO), a solvent, by dehydration without chemical modification, filtered, and subsequently pressed through spinning nozzles. The such formed filaments, after passing an air gap, are precipitated in a bath with an aqueous NMMO-solution and are subsequently cut to staple fibers.

Especially for applications, wherein a product comes into physical contact with a user (as it is the case for clothing, cosmetics or medical technology products), it is important to ensure a reliable quality of products which comprise cellulose.

SUMMARY

It is an object of the present invention to ensure a reliable quality of products which comprise cellulose.

This object is solved by the subject matters according to the independent patent claims. Preferred embodiments result from the dependent patent claims.

According to an embodiment of the present invention, a method of identifying a product which comprises cellulose (wherein the product may comprise a, further in particular regenerated cellulosic, molded body) is provided, wherein in the method a data set is determined which is indicative for multiple constituents of the product or a preform of the product, and the data set which is correlated with the product or the preform is stored in a database.

According to another embodiment, an information which is measured and stored in a database, with respect to at least one intrinsic non-cellulosic constituent (in particular an information with respect to a combination concerning multiple intrinsic non-cellulosic constituents) of a cellulose product which is manufactured from recycled old clothes or a molded body which is manufactured from the cellulose product, is used as a code for identifying an origin of the cellulose product or the molded body.

In the context of this application, the term "cellulose" may in particular denote an organic compound which is a constituent of plant cell walls or can be manufactured synthetically. Cellulose is a polysaccharide (i.e. a multiple sugar). Cellulose is unbranched and typically comprises multiple hundred up to ten thousands β-D-glucose molecules (β-1, 4-glycosidic linkage) and cellobiose-units, respectively. From cellulose molecules, cellulose fibers are built by plants in a controlled manner. By means of a technical process, cellulose molecules can be agglomerated under formation of regenerated fibers, for example as tearproof fibers.

In the context of this application, the term "constituents of the product" may in particular denote different materials and components or constituents, respectively, of the product which comprises cellulose, which are distinguishable by measurement. The constituents of the product on the one hand may be dependent from a starting material for manufacturing a product and on the other hand may be dependent from a method of manufacturing the product. The combination of the constituents and their amounts of a product may thus be indicative for a very certain product or a very certain batch of the product or a preform of the same which was manufactured on the basis of certain starting materials with a certain method. Such a constituent may for example be a main constituent of the product or the preform (for example cellulose which may have different fiber geometries—compare FIG. 3 to FIG. 5—and which may be spectroscopically distinguishable due to different product compositions of the used cellulose sources, for example by a crystallinity determination via NMR). However, such a constituent may also be a foreign matter which is also contained in the final product as a result of using certain starting materials and cellulose sources, respectively (for example polyester and elastane, respectively, in the case of the recycling of old clothes). A constituent may also be a trace element which goes back to a cellulose source and a starting material, respectively (for example titanium dioxide or a rare earth metal). Moreover, it is also possible that a constituent of the product is analyzed which was not yet contained in the starting material and the cellulose source, respectively, but which was added to the product only during or after manufacturing the cellulose fibers or another cellulosic molded body, for example a colorant marker.

In the context of this application, the term "data set" may in particular denote (for example electronically storable) data, whose data content, for multiple constituents, specifies their presence and absence, respectively, in a product or its preform, or even their amount in a product or its preform. For example, the data set may comprise a sequence of logical values "1" and logical values "0", therefore a binary code and a binary sequence, respectively, which, with respect to a certain product or the preform, specifies the fulfillment or non-fulfillment of a respective criterion which is in connection with a certain constituent. For example, one bit of such a data set may specify, whether a product has a concentration of a metal oxide above (corresponding to a logical value "1") or below (corresponding to a logical value "0") a pre-given threshold value. In this way, with a compact data structure, a fingerprint of a certain product or its preform on basis of its constituents can be represented.

In the context of this application, the term "database" may in particular denote an entity of data sets (which may for example be stored on a data storage, further in particular an electronic mass storage (for example a hard disk)). Such a database may be arranged locally at a device for manufacturing products and molded bodies, respectively, which comprise cellulose, or at a remote position, for example cloud-based.

In the context of this application, the term "preform of the product" may in particular denote an intermediate product (in particular also a half-finished product) which is obtained during manufacturing the product (in particular a final product which is intended for use by a consumer) and, after a further processing, may be transferred to the product. The preform and the product may at least partially have the same material composition and/or may be formed at least partially from the same constituents. For example, the product may be a jeans and an associated preform may be a cellulose-fiber or another molded body (in particular a regenerated cellulosic molded body) from which the jeans is manufactured.

According to an exemplary embodiment of the invention, an encoding system for cellulose products is provided, wherein after manufacturing such a product or a preform of it, an information about preferably multiple constituents of this special product or the preform of it is determined by measurement and stored as a data set. This data set may be assigned to this special product or the preform of it. This procedure may be repeated for many products and/or a preforms. The data set for a certain product or its preform is significantly dependent from the starting materials (for example wood, remains from the clothing manufacture, old clothes, natural cotton, etc.) for manufacturing the cellulosic product or the preform, and from the used manufacturing method (for example lyocell-method or viscose-method). For example, when inhomogeneous mixed textiles to be recycled are completely or partially utilized as starting materials, whose material composition varies considerably for different batches, for each product and each preform, respectively, an individual fingerprint of the starting materials and the manufacturing method in form of the data set can be stored. A textile may in particular be a processed fiber product. A mixed textile may correspondingly be denoted as inhomogeneous fiber product. When to a later point in time, for example due to reasons of quality assurance, the originality of a certain test product shall be tested, the same parameters can be determined by measurement again and a best accordance (for example in the sense of a best-match-method) between the determined parameter values of the test product and one of the stored data sets can be searched. In the data set which is assigned to a certain product, the product identity is thus encoded. As according to an exemplary embodiment, a multiplicity of constituents is added to the associated data set, the probability for a false match (i.e. a product is associated to a wrong data set by mistake) can be significantly reduced.

It is especially advantageous to store a combination of multiple intrinsic non-cellulosic constituents of a cellulose product which is manufactured from recycled old textiles as fingerprint of a certain product or a product-preform as associated data set in a database and to compare it with a test product, if required. An intrinsic constituent may in this context in particular denote a constituent of the product or the preform, which, as a result of a used starting material (preferably old textiles) and a used manufacturing method, without additional measures, is unavoidably contained in the final product or also in a preform of it. Thereby, the data set is generatable practically without additional effort, since the constituent which is used as marker does not mandatorily have to be separately added to the product, and nevertheless may be specifically indicative for a very special product (since at old textiles, inhomogeneous mixed textiles can be assumed). By the fact that, as analyzed constituents, not or at least not only the cellulose itself is used, but at least also non-cellulosic foreign matters which originate from the old textiles, a very especially specific and individual, respectively, data set for a certain product may be stored and compared with test products. In this way, it is possible to ensure a reliable quality of products which comprise cellulose, by verifying the origin of the product and the originating from a recycling method, respectively, and falsifications or plagiarism can be reliably identified. In this way, a traceability is enabled also for cellulose products (for example clothes), without the need to take measures which can not or can only hardly be utilized for cellulose products (such as attaching a barcode or RFID-tags).

In the following, additional embodiments of the method and the use are described.

According to an embodiment, the determined data set may be indicative for whether the product or the preform was at least partially manufactured on basis of a recycled cellulose source as starting material for manufacturing the product or the preform. In the context of this application, the term "cellulose source" may in particular denote a medium (in particular a solid body medium) which, as basis for manufacturing a molded body which comprises cellulose, during a corresponding manufacturing method, provides the cellulose material used for this purpose. An example is wood and wood pulp, respectively. Other examples for a recycled cellulose source are textile waste to be recycled, such as post-consumer old clothes, or pre-consumer remains from the textile manufacturing. When using a material to be recycled as starting material and cellulose source, respectively, for manufacturing the product which comprises cellulose, or its preform, in the manufactured product or the preform of the product are unavoidably substances which were contained in the cellulose source. For example, when the cellulose source is made of old clothes, synthetic plastics, such as polyester or elastane, may be present at and/or in the manufactured cellulose fibers. Such synthetic plastics are used in clothes in form of seams, buttons and additives to cellulose fibers, respectively. Since in the recycling of old clothes or the like, frequently inhomogeneous mixed textiles are used (the old clothes which are respectively available do not have a constant composition, instead usually a mixture which is presently available is further processed), in the mentioned application, the composition of a manufactured product which comprises cellulose is significantly different from batch to batch. A composition of multiple constituents of the product or the preform which was detected by measurement after manufacturing such a product or a preform may therefore be used as marker information, also for the mentioned batch and for the originating of a product or a preform (for example a molded body) from a certain company and a certain manufacturing device, respectively. The use of cellulose sources by way of the recycling of mixed textiles thus provides advantages which are special and utilizable without additional effort in connection with the provision of an encoding system for products which comprise cellulose.

According to a preferred embodiment, the product or the preform may be manufactured at least partially on basis of old clothes as cellulose source as starting material for manufacturing the product or the preform. For example, at the starting material, at least 3 weight percent, in particular at least 10 weight percent, further in particular at least 50 weight percent, with respect to the total weight of the starting material may be used. Especially advantageously, for manufacturing the product, recycled old textiles may comprise or consist of items of clothing which have been worn by a user. Such an embodiment is especially preferred, since old clothes frequently comprise an especially inhomogeneous composition with significant portions of foreign matters which may be used as intrinsic non-cellulosic constituents of the product to be manufactured as markers. In the context of this application, the term "old clothes" may denote clothes, in particular comprising cellulose, which have been already used (in particular worn) by a user when at least a part of the cellulose is recovered. Thus, old clothes may be a starting material comprising cellulose which may (but does not have to) comprise a substantial amount of foreign matters and which may be used for recovering cellulose, after a user has used the old clothes as clothing or in any other way. In particular, old clothes may be made of a mixture of cellulose and one or more foreign matters, in particular comprising (in particular frequently used in clothing) synthetic plastic (as polyester and/or elastane, for example) and/or foreign matters which are separate and do not comprise cellulose (such as buttons, textile print or seams). Polyester may in particular denote polymers with ester functions (R—[—CO—O—]—R) in their main chain. Polycarbonates and polyethylene terephthalate belong to polyesters. Elastane in particular denotes an extensible chemical fiber with a high elasticity. A block copolymer which is underlying elastane may contain 85% by weight polyurethane.

According to an embodiment, the product or the preform may alternatively or in addition at least partially be manufactured on basis of remains of a clothing manufacture as cellulose source as starting material for manufacturing the product or the preform. In the context of this application, the term "remains from a clothing manufacture" may in particular denote waste and/or offcut of a textile or yarn which comprises or consists of cellulose, wherein said remains occur during a method of manufacturing clothes. In the manufacture of clothing, for example a textile which comprises cellulose is manufactured as starting material, from which planar parts (for example in form of a half T-shirt) are cut. Remains are left, which can be resupplied to a method of manufacturing a molded body which comprises cellulose, according to an exemplary embodiment. Thus, remains from a clothing manufacture may be a starting material which comprises or consists of cellulose, which can be used for recovering cellulose before a consumer has used the remains as clothes or in any other way. In particular, the remains from a clothing manufacture may be made of substantially pure cellulose, in particular without foreign matters which are separate and do not comprise cellulose (as buttons, textile print or seams, for example).

According to an embodiment, the product or the preform may at least partially be manufactured on basis of a further cellulose source, in particular on basis of at least one material of a group which is consisting of wood pulp, rags pulp (in particular pulp of textile remains, such as offcut remains, etc.), cotton (i.e. cellulose from a cotton plant), cellulose manufactured by a lyocell-method, and cellulose manufactured by a viscose-method. Thus, it is also possible to provide only a part of the starting material in form of old clothes and remains from the textile manufacture, respectively. The starting material may also be an inhomogeneous mixed tissue which further improves its suitability as encoding marker. The rest of the starting material, which is not supplied in form of old clothes and remains from the textile manufacture, respectively, may be supplemented flexibly and depending on availability by one or more other cellulose sources. Thereby, the industrial utilization of the manufacturing method is not impaired by possible temporal bottlenecks of old clothes and remains from the textile manufacturing, respectively. Instead, it is for example possible to compensate and balance out, respectively, possible missing quantities of cellulose from textiles to be recycled by another cellulose sources. Preferably, forming the starting material may be exclusively performed from old clothes, since their properties as inhomogeneous mixed textile are especially advantageous for an intrinsic encoding system according to an exemplary embodiment.

According to an embodiment, the product or the preform may be manufactured on basis of a starting material which is manufactured as inhomogeneous (and optionally temporarily variable over a period of one or more manufacturing methods) mixture of different constituents. Exactly this inhomogeneity which occurs due to unpredictable properties of incoming material to be recycled as starting material, may be advantageously used, according to an exemplary embodiment, for the purpose that also different products and preforms, respectively, due to the inhomogeneous starting materials, at least with respect to foreign matters, significantly deviate from each other, such that exactly this foreign matters can be utilized with advantage for encoding and identifying, respectively, products and its preforms.

According to an embodiment, the product or the preform can be manufactured by the lyocell-method or by the viscose-method. Both in the lyocell-method (compare FIG. 3) and in the viscose-method (compare FIG. 4), characteristic geometric properties can be impressed to cellulose fibers. Therefore, the fiber shape of cellulose in the manufactured product, as part of the data set and an associated bit sequence, may be a part of the code and fingerprint, respectively, of a product from a certain batch and from a certain manufacturing device.

In the context of this application, the term "lyocell-method" may in particular denote a method of manufacturing cellulose according to a direct solvent method. The cellulose for the lyocell-method can be obtained from a starting material which contains said cellulose. In the lyocell-method, the starting material can be solved in a suitable solvent (in particular comprising tertiary amine oxides, such as N-methylmorpholine-N-oxide (NMMO) and/or ionic liquids, i.e. low-melting salts made of cations and anions). Solving may be performed in particular by dehydration and/or without chemical modification. The obtained solution, which may be also denoted as dope or spinning solution, may subsequently be pressed through one or more spinning nozzles in the lyocell-method. Thereby formed filaments can be precipitated during and/or after their free or controlled fall through an air gap in a water containing bath (in particular in a bath with aqueous NMMO-solution) and/or in the air humidity present in the air gap.

In the context of this application, the term "viscose-method" may in particular denote a method of manufacturing cellulose according to a wet spinning method. The cellulose for the viscose-method can be obtained from a starting material (in particular wood or a wood pulp) which contains said cellulose. In subsequent process stages in the viscose-method, the starting material can first be treated with a base (for example caustic soda), whereby alkali cellulose is formed. In a subsequent conversion of said alkali cellulose with carbon disulfide, cellulose-xanthagonate is formed. From this, by a further supply of a base (in particular caustic soda), a viscose-spinning solution can be produced which can be pressed through one or more spinning nozzles. In a spinning bath, viscose-filaments are generated by coagulation.

According to an embodiment, in the method, a test product may be analyzed for determining an information which is indicative for multiple constituents of the test product, and the information may be compared with the data set in the database. Such a test product may for example be a product which, during its distribution process and using process, shall be tested with regard to its authenticity and its origin, respectively. This may be desirable for example for clarifying the issue of the originality of the product or its preform from a certain source, for assigning a product or its preform to a certain manufacturing process (in particular to a certain batch), for retracing a product or its preform over its lifetime, for clarifying whether a product or its preform originates from a recycled cellulose source, etc.

According to an embodiment, in the method, at least one other data set can be determined which is indicative for multiple constituents of at least one other product or a preform of the at least one other product, and the data set which is correlated with the at least one other product or its preform may be stored in the database. In other words, for many or even all manufactured products and preforms, respectively, data sets can be determined and stored in the database in connection with a respective product. For a later identification of a test product as associated with one of the data sets, many comparative data can then be used and the reliability of an assignment can therefore be improved. In other words, by such a complex set of many data sets, the information basis for the assignment of the test product is enlarged.

According to an embodiment, the information can be compared with the data sets and the test product can be identified as associated with one of the data sets, when a discrepancy between the information on the one hand and one of the data sets on the other hand falls below or does not exceed a pre-given threshold value, in particular a number of not fulfilled bit criteria (preferably not a single bit criterion). An alternative decision criterion, whether one of the data sets is in accordance with a test product, consists of that an identity can be assumed, when the information and this data set show a highest possible accordance (in particular a better accordance than all other data sets). For example, a highest possible accordance may correspond to a highest number of accordant bit criteria (preferably an accordance with respect to all bit criteria). When a test product shall be identified and its origin shall be retraced, respectively, the test product can be made subject to the same measurement by which the respective data sets for the products and the preforms, respectively, were obtained. For example, such an elucidation of the multiple constituents and their properties (for example their amount or their presence or absence) in a test product may be performed by a spectroscopic analyze (for example by mass spectrometry). A such obtained test data set for the test product may be equilibrated and compared, respectively, with the data sets which are stored in the database. For this purpose, multiple criteria can be applied which may be in connection with the analyzed constituents. For example, the criterion may be applied, whether a rare earth can be determined in the test product, or whether a certain rare earth could be detected in the test product with a certain minimum concentration or within a pregiven concentration range. As a result of applying these criteria to the test product and by a corresponding comparison with the application of these criteria to the products and the preforms, respectively, according to the data sets, for each criterion, for example an associated bit value may be defined with advantage (for example a logical value "1", if the respective criterion is fulfilled, or "0", if the respective criterion is not fulfilled). Thereby, with a very low requirement to memory-technical and processor-technical resources, and consequently very fast, a comparison of the bit values and a bit sequence built therefrom, respectively, can be performed. As result of this calculation operations, a data set may be extracted from the database, which yielded a best accordance with a data set of the test product. An assignment of a test product to a certain product (or to a preform of the product) for which previously an associated data set was stored, is thus possible in an error-robust manner.

According to an embodiment, the data set may be indicative for a combination of constituents which are present in the product, in particular for a combination of constituents which are contained in the product with a certain amount. The higher the number of the constituents which are added to the data set, the more meaningful is the result of an assignment between a product corresponding to a data set and a test product to be tested. For example, the number of constituents, to which a corresponding criterion or a corresponding value is stored in the database, may be at least three, in particular at least four, further in particular at least six, preferably at least eight. The higher the number of constituents, the lower is the risk that a test product is assigned to a false data set.

According to an embodiment, the multiple constituents may, in particular exclusively, relate to non-cellulosic constituents of the product or the preform. "Non-cellulosic constituents" may here denote constituents and constituents of the product or the preform, respectively, which are different from cellulose (in particular lyocell-cellulose, viscose, and cotton cellulose). These non-cellulosic components may be in particular foreign matters which were contained in the starting material (for example rare earths, metal oxides, synthetic plastics, colorants, etc.) or which were not yet contained in the starting material and which have been added to a later point in time during manufacturing the product as external or extrinsic marker (for example a coating made of luminophores). As (in particular extrinsic) markers, also shape-selected particles may be used, for example cube-shaped, sphere-shaped, and/or tetrahedron-shaped nanoparticles. Since such foreign matters are uncharacteristic and unspecific for cellulose products, without impairing the quality of the products and the preform, respectively, they are especially suitable as marker or encoding substances for unambiguously identifying a certain product or at least a certain product batch.

According to an embodiment, the multiple constituents may, in particular exclusively, relate to intrinsic constituents of the product or the preform which, already after a coagulating of filaments which comprise cellulose from a spinning solution, were contained in and/or at and/or between the filaments. In particular, the intrinsic constituents may have been already contained in and/or at the molded bodies after an extrusion of a spinning solution to cellulosic molded bodies. "Intrinsic constituents" may here in particular denote constituents of the product or the preform which were already contained in the starting material and the cellulose source, respectively, for manufacturing the product or the product-preform. Due to the practically high inhomogeneity with respect to the composition of recycling-starting materials, intrinsic constituents are highly suitable for using as encoding marker, and this without any additional effort.

According to an embodiment, the intrinsic constituents and/or the non-cellulosic constituents may comprise at least one of a group which is consisting of a trace element (i.e. a constituent which is only contained in a very low portion), in particular a metal, further in particular a rare earth metal, a metal oxide, in particular titanium dioxide and/or zinc oxide, a colorant, a luminescent material, and a synthetic plastic, in particular elastane and/or polyester. Other intrinsic constituents are possible, dependent from the composition of a starting material, and may, especially when old clothes are used as inhomogeneous mixed textile, with advantage vary significantly in different product batches with respect to type and amount.

According to an embodiment, at least one of the multiple constituents may relate to at least one cellulosic constituent of the product or the preform. A "cellulosic constituent" may in particular denote a component and a constituent, respectively, of the product or the preform which concerns the cellulose of it (in particular cellulose which is regenerated according to the lyocell-method or the viscose-method, cotton cellulose and/or wood pulp). Cellulose may differ in different products, different preforms or in different product constituents with respect to the geometric form of appearance (compare FIG. 3 to FIG. 5). Also the chemical properties of cellulose and its elements (in particular carbon) may differ due to the chemical environment which is different in different products. This may be differentiated in form of different displacement values in an NMR spectrum, for example. The data base comparison may thus also deliver an information about a fiber type of a product or a preform.

According to an embodiment, the intrinsic constituents and/or the non-cellulosic constituents may origin completely or partially from old textiles. Due to the high inhomogeneity and the changing composition of old textiles as starting material to be recycled for manufacturing the cellulose-containing product, its foreign matter composition is an especially individual marker which encodes a certain product and reliably differs from other products or at least product batches.

According to an embodiment, the method may comprise, during or after a manufacturing of the product or its preform (in particular after a coagulating of filaments which comprise cellulose from a spinning solution), combining the product or a preform with at least one extrinsic constituent for which the data set which is stored in the database is also indicative. An external or extrinsic constituent which was not yet contained in the cellulose source as starting material for manufacturing of the product and the preform, respectively, may thus be specially added to the product for further refining the encoding accuracy. Combining the finished manufactured cellulose of the product or the preform with an extrinsic constituent (for example a luminophore or the like) may, alternatively or preferably in addition to measuring at least one intrinsic constituent of the product or its preform, further improve the distinguishability of the product from other products. Such an extrinsic constituent (or multiple) may be added to different products or preforms in the same or preferably in different amounts with respect to type and/or amount (for example as pigment which is incorporated in the molded body) in order to further refine and to diversify, respectively, the data set.

According to an embodiment, the data set can be assigned to a product batch. According to such an embodiment, it is sufficient to store commonly for all products of a product batch (for example all products which are manufactured at one day at the same manufacturing device) a data set. This keeps the data amount to be managed low and furthermore enables a very specific characterizing of the product with respect to its origin.

Figure 2:
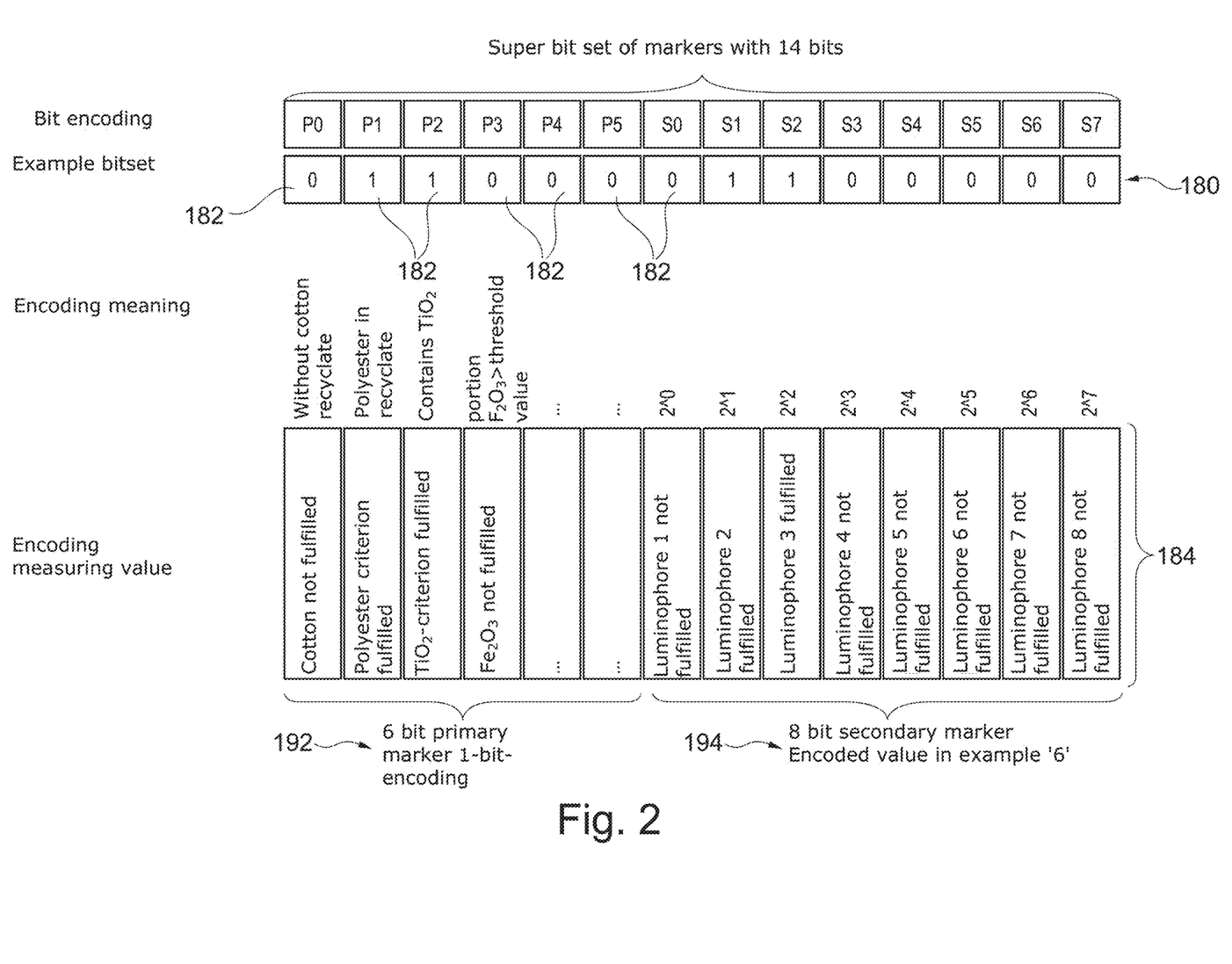
FIG. 2 shows a bit sequence of a data set which identifies a product with a cellulose fiber manufactured by a lyocell-method.

According to an embodiment, in the method, a bit sequence which is indicative for a composition of the product or its preform made of the at least two constituents may be stored as data set in the database (compare FIG. 2). The longer the bit sequence, the higher is the reliability of the assignment of a data set to a test product.

According to an embodiment, the product or its preform may be a molded body or may be manufactured on basis of a molded body. In the context of this application, the term "molded body" may in particular denote a two-dimensional or three-dimensional geometric body which is a result of a method of manufacturing and recovery, respectively, of cellulose. In particular, a molded body denotes a two-dimensional or three-dimensional object which comprises cellulose or consists of it and is manufactured from solved pulp. In particular, the molded body may be a regenerated cellulosic molded body. Molded bodies may be in particular lyocell-molded bodies, viscose-molded bodies or modal-molded bodies. Typical molded bodies are filaments, fibers, sponges and/or films. Basically, all types of cellulose molded bodies are suitable for embodiments of the invention. Both endless filaments and cut staple fibers with conventional dimensions (for example 38 mm length) and short fibers are considered as fibers. For manufacturing fibers, both methods with withdrawing devices downstream of one or more extrusion nozzles, and also other methods, as in particular melt-blowing-methods, are possible. Alternatively to fibers, a foil which comprises cellulose can be manufactured as molded body, i.e. a planar and substantially homogenous film with or made of cellulose. Foils may be in particular manufactured by adjusting the process parameters of a lyocell-method such that coagulating is at least partially triggered only after the filaments impinge on a receiving surface. Planar cellulose molded bodies are considered as foils, wherein the thickness of these foils is adjustable (for example by selecting a number of serially arranged nozzle beams). Other embodiments of a molded body are a tissue and a fleece made of cellulose filaments and cellulose fibers, respectively, in particular a spinning fleece made of integrally merged ("merging") substantially continuous cellulose filaments ("melt blown"). Here, in particular a textile planar structure made of at least two (preferably orthogonal or almost orthogonal) crossed thread systems (or fiber systems) may be considered as a tissue, wherein threads (or fibers) in longitudinal direction may be denoted as warp threads and threads (or fibers) in a transverse direction may be denoted as weft threads. A fleece or nonwoven may be denoted as disordered (in particular present in random orientation) structure of filaments or fibers or cut yarn with limited length which are joined together to a fiber layer or a fiber web and which are connected to each other (in particular in a frictionally engaged manner). A molded body may also be created in the form of a sphere. As molded body, also cellulose-comprising particles, as in particular beads (i.e. a granulate and spherules, respectively) or flakes may be provided which can be further processed in this form. Thus, possible cellulose molded bodies are also particulate structures as granulate, spherical powder or fibrids. A shaping of a molded body is preferably performed by extrusion of a spinning solution which contains cellulose through an extrusion nozzle, since large amounts of cellulose molded bodies with a very uniform shape can be manufactured in this way.

A further possible cellulose molded body is a sponge or, more general, a porous molded body. According to exemplary embodiments, the mentioned molded bodies can be used for manufacturing yarns, textiles, gels or composite materials, for example.

The molded bodies manufactured according to the invention may be used as packaging material, fiber material, textile composite materials, fiber composite materials, fiber fleeces, needle felts, quilting cotton, tissues, knitted fabrics, as home textiles such as bedclothes, as clothes, as filling textile, flocking substance, hospital textiles such as underlays, diaper or mattresses, as fabric for heating blankets, shoe inserts and wound dressings. Embodiments of the invention may be applicable in both different technical fields and in medicine and in cosmetics and wellness. In medicine, for example materials for wound treatment and wound healing may be made of a carrier which determines the mechanical properties and a biocompatible coating material which is especially compatible with the skin and with the surface of the wound.

Many other applications are possible.

BRIEF DESCRIPTION OF THE DRAWINGS

In the following, exemplary embodiments of the present invention are described in detail with reference to the following figures.

DETAILED DESCRIPTION

Same or similar components in different figures are provided with the same reference numbers.

Before, referring to the figures, exemplary embodiments are described, some basic considerations shall be summarized based on which exemplary embodiments of the invention have been derived.

According to an exemplary embodiment of the invention, an encoding system for cellulose products is provided, in particular manufactured by a lyocell-method. In this way, a forgery-proof fiber (as molded body or product-preform) and a forgery-proof product based on this fiber, respectively, can be provided, since an alleged plagiarism, by means of the encoding system, can be simply and reliably tested for authenticity. In more detail, according to an exemplary embodiment, a system is provided by whose assistance in particular cellulosic lyocell-fibers can be correspondingly marked, such that, for example an end-user is enabled to test an alleged lyocell-fiber (in particular manufactured by recycling of old clothes) for authenticity by a testing device (for example a special measuring device. For example, a bit sequence may be generated and stored, which encodes characteristic data of a fiber and a corresponding product, respectively. With advantage, the bits may be presented by independent, physically measurable variables. For example, the bits may be set by the presence of certain substances which are usually not present in textile planar structures (such as rare earth metals, etc.). Alternatively or in addition, also residual substances which are not removed from recycling materials in a residue-free manner can be utilized for marking. For example, a certain bit sequence at recycling-residues can be utilized for labeling lyocell-fibers with a recycling-portion.

According to an embodiment, for example a marking of lyocell-fibers can be mapped via a code, for example in form of a bit sequence, such that a traceability of the fibers up to the finished textile product is possible. Thereby, a reliable forgery-protection, in particular of lyocell-fibers, can be achieved.

Figure 1:
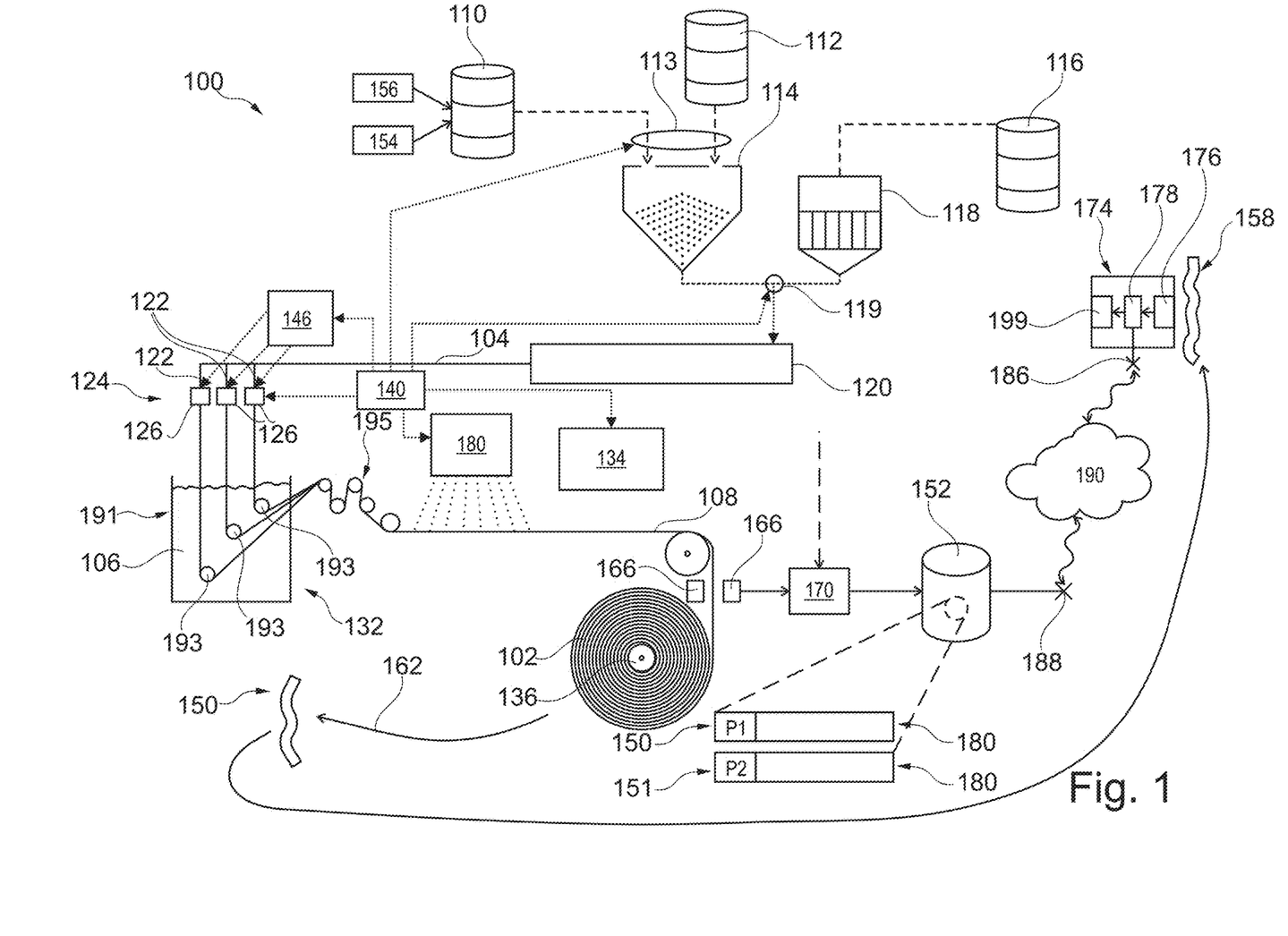
FIG. 1 shows a device for manufacturing a molded body which comprises cellulose by a lyocell-method, and for subsequently identifying a correspondingly manufactured product which comprises cellulose during its lifetime according to an exemplary embodiment of the invention.

FIG. 1 shows a device 100 for manufacturing a molded body 102 which comprises cellulose by means of a lyocell-method and for subsequently identifying a correspondingly manufactured product 150 which comprises cellulose, during its lifetime according to an exemplary embodiment of the invention.

Thus, FIG. 1 shows a device 100 according to an exemplary embodiment of the invention for manufacturing a cellulose-comprising molded body 102 which may be manufactured in form of a fleece (nonwoven), as fiber, foil, sphere, textile tissue, sponge, or in form of beads or flakes, for example. According to FIG. 1, the molded body 102 is manufactured directly from a spinning solution 104. The latter is converted to cellulose fibers 108 as molded body 102 by means of a coagulation-fluid 106 (in particular made of air humidity) and/or a coagulation-bath 191 (for example a water bath which optionally comprises tertiary amine oxides such as N-methylmorpholine-N-oxide (NMMO)). By means of the device 100, a lyocell-method may be performed. In this way, substantially endless filaments or fibers 108 or mixtures of substantially endless filaments and fibers 108 with a discrete length may be manufactured as molded body 102, for example. A plurality of nozzles which respectively have one or more openings 126 (which may be also denoted as spinning holes) are provided for ejecting the lyocell-spinning solution 104.

As can be taken from FIG. 1, a starting material 110 which is based on cellulose may be supplied to a storage tank 114 via a dosing device 113.

According to an embodiment, a water ingress in the cellulose-based starting material 110 may be performed by a solvent 116 (in particular NMMO) which is described in more detail below. The cellulose-based starting material 110 itself may also contain a certain residual moisture (dry pulp frequently has a residual moisture of 5 weight percent to 8 weight percent, for example). In particular, according to the described embodiment, the starting material 110 may directly be supplied to a mixture of water and solvent 116 without pre-moistening. An optional water container 112 which is shown in FIG. 1 may then be omitted.

According to an alternative embodiment, the starting material 110 which is comprising cellulose may be additionally moistened, in order to therefore provide moist cellulose. For this purpose, water from an optional water container 112 may be supplied to the storage tank 114 via the dosing device 113. Therefore, the dosing device 113 which is controlled by a control device 140 may supply adjustable relative amounts of water and starting material 110 to the storage tank 114.

A suitable solvent 116, preferably tertiary amine oxides, such as N-methylmorpholine-N-oxide (NMMO), and an aqueous mixture of the solvent 116, respectively, for example a 76% solution of NMMO in water, is contained in a solvent container. The concentration of the solvent 116 may be adjusted in a concentrating device 118 either by supplying pure solvent or water. The solvent 116 may then be mixed with the starting material 110 with definable relative amounts in a mixing unit 119. Also the mixing unit 119 may be controlled by the control unit 140. Thereby, the cellulose-comprising starting material 110 is solved in the concentrated solvent 116 in a solving device 120 with adjustable relative amounts, whereby the lyocell-spinning solution 104 is obtained. The relative concentration ranges (also denoted as spinning window) of the components starting material 110, water, and solvent 116 in the spinning solution 104 for manufacturing cellulosic regenerated molded bodies according to the lyocell-method may be suitably adjusted as known to a person skilled in the art.

The lyocell-spinning solution 104 is supplied to a fiber generating device 124 (which may be configured with a number of spinning beams or jets 122).

When the lyocell-spinning solution 104 is guided through the openings 126 of the jets 122, it is separated into a plurality of parallel threads made of the lyocell-spinning solution 104. The described process flow transforms the lyocell-spinning solution 104 to increasingly long and thin threads whose properties may be adjusted by a corresponding adjustment of the process conditions, controlled by the control unit 140. Optionally, a gas flow may accelerate the lyocell-spinning solution 104 on its way from the openings 126 to a fiber receiving unit 132.

After the lyocell-spinning solution 104 has moved through the jets 122 and further downwards, the long and thin threads of the lyocell-spinning solution 104 interact with the coagulation-fluid 106.

In the interaction with the coagulation-fluid 106 (for example water), the solvent concentration of the lyocell-spinning solution 104 is reduced, such that the cellulose of the starting material 110 at least partially coagulates and precipitates, respectively, as long and thin cellulose fibers 108 (which may still contain residues of solvent and water).

During or after the initial formation of the individual cellulose fibers 108 from the extruded lyocell-spinning solution 104, the cellulose fibers 108 are received at the fiber receiving unit 132. The cellulose fibers 108 may immerse into the coagulation-bath 191 shown in FIG. 1 (for example a water bath optionally comprising a solvent such as NMMO) and may complete their precipitation when interacting with the liquid of the coagulation-bath 191. Depending on the process adjustment of the coagulation, the cellulose may form cellulose fibers 108 (as shown, wherein the cellulose fibers 108 may be made of one substance and integrally merged with each other ("merging"), respectively, or may be present as separated cellulose fibers 108), or a foil and a film, respectively, made of cellulose may form at the fiber receiving unit 132 (not illustrated in FIG. 1).

Thus, the cellulose fibers 108 are extruded out of the spinning nozzles of the jets 122 and are guided through the spinning bath and coagulation-bath 191, respectively (for example containing water and NMMO in low concentration for precipitation/coagulation), wherein the cellulose fibers 108 are guided around a respective deflection roll 193 in the coagulation-bath 191 and are supplied to a draw-off godet outside the coagulation-bath 191. The draw-off godet 195 serves for further transport and post-stretching of the cellulose fibers 108, in order to achieve a desired titer. Downstream the draw-off godet 195, the fiber bundle made of the cellulose fibers 108 is washed in a washing unit 180, optionally scrooped and subsequently cut (not shown).

Although not illustrated in FIG. 1, the solvent 116 of the lyocell-spinning solution 104 which is removed from the cellulose fibers 108 when coagulating and in a subsequent washing in the washing unit 180, may be at least partially recovered and recycled, respectively, and may be transferred back in the storage tank 114 in a subsequent cycle.

During the transport along the fiber receiving unit 132, the molded body 102 (here in form of the cellulose fibers 108) may be washed by means of the washing unit 180, as the latter supplies a washing liquid for removing solvent residues. Thereafter, the molded body 102 may be dried.

Moreover, the molded body 102 may be made subject to a posttreatment, see the schematically illustrated posttreatment unit 134. For example, such a posttreatment may comprise a hydro-entangling, a posttreatment, a needle treatment, an impregnation, a steam treatment with a steam which is supplied under pressure and/or a calendaring, etc.

The fiber receiving unit 132 may supply the molded body 102 to a winding device 136, at which the molded body 102 may be winded. The molded body 102 may then be supplied as rolling freight to an entity which manufactures products such as wipes or textiles on basis of the molded body 102.

The molded body 102 may then be directly used or may be further processed to a certain product 150 (for example a textile tissue) in a manner which is schematically illustrated with reference sign 162 in FIG. 1. During the lifetime of such a product 150, it may occur that the product 150, whose originality and origin, respectively, is doubted or shall be determined and tested, respectively, shall be retraced. In the following, a system and a method of identifying such a product 150 which comprises cellulose according to an exemplary embodiment of the invention is described.

At first, optionally during manufacturing the product 150 (more specifically after coagulating the cellulose-comprising filaments for forming the cellulose fibers 108 from the spinning solution 104), the product 150 may be combined with an extrinsic constituent 160, for example a luminophore, at a marking unit 164 which is controlled by the control unit 140.

The product 150 which is combined with the extrinsic constituent 160 or (as illustrated in FIG. 1) a preform of the product 150 in form of the molded body 102 may be measured at a measuring unit 166. For example, the measuring unit 166 may comprise a spectrometer (for example a mass spectrometer, an NMR-spectrometer, etc.) by which the product 150 or the preform in form of the molded body 102 may be examined by measurement and characterized with respect to its composition made of multiple substances.

In the measuring unit 166, the product 150 or its preform may thus be measured with respect to a combination of components and constituents, respectively, which are present in the product 150 or in the preform, with respect to the type and the amount. The tested constituents may completely or partially be non-cellulosic constituents of the product 150 or the molded body 102. As non-cellulosic constituents of the product 150 or its preform which are analyzed qualitatively or quantitatively, single trace elements, in particular metals, further in particular a rare earth metals, metal oxides, such as titanium dioxide and zinc oxide, respectively, a colorant (for example indigo from denim-products), a luminescent and synthetic plastic, such as elastane and polyester, respectively, may be examined. Such non-cellulosic constituents may origin from post-consumer-old textiles which have been used during the above described manufacturing method in form of a cellulose source 154 as part of the starting material 110. Such old textiles frequently contain the mentioned and other foreign matters which thus can also be found in the product 150 and the molded body 102, respectively.

Also one (or more) further cellulose source 156 which may be additionally supplied to the old textiles as part of the starting material 110 may contain such foreign matters. Therefore, the constituents which are measured by the measuring unit 166 in the product 150 or its preform in form of the molded body 102 may relate to intrinsic constituents of the product 150 or the preform, which were already contained in the starting material 110 and consequently in the formed cellulose fibers 108.

Also at least one cellulosic constituent of the product 150 or its preform can be measured by the measuring unit 166, in order to characterize the product 150 and its preform in form of the molded body 102, respectively.

Furthermore, additionally the optional extrinsic constituent 160 may be measured by the measuring unit 166.

As result of the measurement of the measuring unit 166 at a certain product 150 and its preform in form of the molded body 102, respectively, a data set 180 which is correlated with the product 150 and its preform, respectively, may be stored in a database 152. The database 152 may comprise data sets 180 and other data which may for example be stored on an electronic mass storage or a part of an electronic mass storage, such as a hard disk of a computer. In this database 152, a multiplicity of data sets 180 are stored which correlate a respective product 150 and its preform, respectively, with the associated measuring result of the measuring unit 166. Each of the data sets 180 contains for an associated product 150 and its preform, respectively, the information with respect to the intrinsic and extrinsic, respectively, non-cellulosic and cellulosic, respectively, constituents. It is also possible that the data set 180 contains an information with respect to the form of appearance of the cellulose fibers 108 (therefore an information about a cellulosic constituent) which are contained in the molded body 102 and in the product 150, respectively. This corresponds, as explained with reference to FIG. 3 to FIG. 5, conclusions to a used method of manufacturing the cellulose fibers 108 (lyocell-method or viscose-method).

An information which is captured by measurement and an information derived therefrom, respectively, may be contained in the respective data set 180 in form of qualitative (constituent present or not present) or quantitative (constituent present at least or at most in a certain amount) data. However, alternatively or in addition, a corresponding information may also be contained in form of logical values with respect to criteria which relate to the mentioned constituents (for example a logical value "0", if a constituent was contained in a product 150 or its preform at least with a pregiven amount, or a logical value "1", if a constituent was not present at least with a pregiven amount in a product 150 or its preform, or vice versa). It is also possible to store the mentioned information in the data set 180 in form of bits, i.e. in binary logic. In particular, the determined data set 180 may therefore be indicative for whether the product 150 was manufactured at least partially on basis of a recycled cellulose source 154 in form of the old textiles as at least a part of the starting material 110.

The mentioned information which is added to the respective data set 180, may be determined on basis of the measuring values of the measuring unit 166 by a processor unit 170. This processor unit 170 may optionally be coupled with the control unit 140 or may form a part of the same.

As schematically illustrated in FIG. 1, in the database 152, in addition to the data set 180 for the product 150 "P1", as a further data set 180 for a further product 151 "P2", in a corresponding manner also for the further product 151, a data set 180 correlating thereto may be stored. In this way, the database 152 may contain with respect to many different products 150, 151, . . . , an associated data set 180. Alternatively, it is also possible that one respective data set 180 in the database 152 is associated with all products 150 of a common production batch and that other products 151 of other production batches are correlated with respectively other data sets 180 in the database 152.

When a user, for a test product 158 (or for a preform of the same), for example for retracement purposes or as proof of origin, would like to know which identity this test product 158 has, or in which batch this test product 158 was produced, the user can measure such a test product 158 with a testing device 174. The testing device 174 may be configured as a portable device, for example. The testing device 174 may comprise a measuring apparatus 176 for measuring the information with respect to the constituents of the test product 158, in the same or similar manner as the measuring unit 166. Thus, the testing device 174 is configured for determining the information which is indicative for multiple constituents of the test product 158. A processing unit 178 of the testing device 174 may process the information captured by the measuring apparatus 176 by measurement. In particular, the processing unit 178, in interaction with a communication unit 186 of the testing device 174, may request data sets 180 from the database 152 by the fact that the communication unit 186 of the testing device 174 communicates with another communication unit 188 connected to the database 152 via a communication network 190 (for example the public internet) and transfers data.

When the processing unit 178 of the testing device 164 has gained access to the data sets 180 of the database 152, the information captured by the measuring apparatus 176 is compared with the data sets 180 in the database 152. For example, the data set 180 of the database 152 is determined which shows the highest possible accordance with the information determined by the measuring apparatus 176 for the test product 158 with respect to its constituents. Thus, for example, identifying the test product 158 as being associated with one of the data sets 180 may be performed, when a discrepancy between the information captured by the measuring apparatus 176 with respect to the test product 158 on the one hand and one of the data sets 180 on the other hand falls below or does not exceed a pregiven threshold value. As a suitable threshold value, in particular a number of fulfilled and not fulfilled, respectively, bit criteria 184 may be used, compare FIG. 2. The product 150, 151, . . . , which is assigned to this best matching data set 180, can be identified as identical to the test product 158 (or at least as associated with the same production batch). In this way, the originality of the test product 158 can be verified and its assignment to a production batch can be enabled. If this identification fails, the conclusion can be drawn that the test product 158 does not originate from the device 100 and possibly constitutes a forgery.

The result of this analysis may be showed to a user at a display unit 199 of the testing device 174. If required, the result of this analysis may also be transferred to the processor unit 170 via the communication network 190.

FIG. 2 shows a bit sequence 182 of a data set 180 which identifies a product 150 with a cellulose fiber 108 which is manufactured by a lyocell-method. Thus, according to FIG. 2, as already described with reference to FIG. 1, as data set 180, a bit sequence 182 which is indicative for a composition of the product 150 made of the diverse constituents is stored and saved, respectively, in the database 152.

Thus, FIG. 2 shows, how in total 14 bits are assigned to a certain product 150 (and an associated preform in form of the molded body 102, respectively) as data set 180. Six bits P0 to P5 relate to certain criteria which are fulfilled or not fulfilled by the product 150 or its preform. In the illustrated embodiment, for example a titanium dioxide criterion (i.e. a criterion concerning an amount of the constituent $TiO_2$) in the product 150 is fulfilled, such that the associated bit has the logical value "1". In contrast, a criterion with respect to iron oxide $Fe_2O_3$ in the product 150 is not fulfilled, such that the associated bit has the logical value "0". Eight further bits S0 to S7 relate to further luminophore-based criteria which are also partially fulfilled and partially not fulfilled by the product 150 or its preform. Thus, the bit sequence 182 of the product 150 (01100001100000 in the illustrated example) is the code for this product 150 and a characteristic fingerprint of the product 150. A test product 158 can be considered as identical to this product 150, when for the test product 158, the same bit sequence (01100001100000 in the illustrated example) is determined.

In the following, some further aspects of exemplary embodiments of the invention are described:

According to an exemplary embodiment, an encoding system for the lyocell-fibers with recyclate portion is provided. Fibers (in particular cellulose fibers 108) which were manufactured by the lyocell-method may be utilized for different applications. The recycling of materials in the sense of a possibly closed substance cycle is a demand in terms of conservation of resources, sustainability and environmental protection. For consumers, a testable feature may be advantageous which confirms the recyclate portion of a product 150, i.e. which enables an examination, whether the product 150 was manufactured on basis of recycled cellulose sources 154, 156. In the context of the present application, the term "recyclate" may in particular denote materials recovered from the substance cycle of the type yarns, textiles or fleeces (i.e. nonwovens) which are used (in particular at the earliest) during the pulp manufacture in the context of the lyocell-method or in the yarn manufacture.

Exemplary embodiments of the invention are, amongst others, based on the knowledge that in the context of the lyocell-production, an identification of the recyclate within the meaning of a quantitative material identification before or during the recyclate processing is desirable and advantageous, respectively. Embodiments of the invention thus provide a marking system for testing whether at least portions of recycled materials are present in a lyocell fiber of a product 150, which can only hardly be forged and is forgery-proof, respectively. In particular, according to an exemplary embodiment, a marking system is provided, wherein different ingredients in a product 150 or a preform are mapping the single bits of a bit sequence 182 of an encoding system for the proof of originality of the corresponding product 150. With advantage, such ingredients and constituents, respectively, may comprise a direct relation to the marked content, whereby an additional self-marking is achieved.

By ingredients or additives for which is ensured that they are present in the dope and a spinning solution 104, respectively, of a lyocell-process in a suitable concentration, a marker system can be formed which enables a binary encoding (compare FIG. 2). By generating a molded body 102 (for example in form of a fiber) which comprises lyocell-cellulose, this marker constituents may be embedded in an interior of the molded bodies 102 and can thus be integrated with a high forgery-protection.

According to exemplary embodiments of the invention, an additional forgery-resistance may be achieved by marker bits which are a partial property of the originality to be proved. For example, purposeful maintaining of portions of a cotton fiber in a recyclate is a more elaborate process than simply using all recyclate in a non-controlled manner. Such portion-related or property-related marker bits at the property to be proven in the end product in combination with marker bits in relation to a qualitative or even quantitative presence of constituents in a product 150 (for example a bit value basis due to the detection of substances or compounds with minimum portions of rare earth, etc.) together form a bit sequence 182 which may also be denoted as super bit sequence. Such a super bit sequence may also the encoding of a sub-information (such as manufacturing date, batch, manufacturer, identifier of a product 150, etc.) together with originality entities of the product 150 which are also integrated via another region of the bit sequence 182 and bit set, respectively.

According to an embodiment, the bit sequence 184 may comprise one or preferably more primary marker bits 192 with contentual and/or functional and/or material respect to a lyocell-based product 150, and one or preferably more secondary marker bits 194 concerning materials with a pure marker character. Such a super bit set which is also illustrated in FIG. 2, is thus preferably composed of secondary marker bits 194 of materials with a pure marker character (for example luminophores) and of primary marker bits 192 which may have a contentual and/or functional and/or material respect to the lyocell-based special product (for example recyclate specialization, natural fibers (for example cotton fibers), optical brighteners, plastics, fluorescing components). The concentration of the primary marker bits 192 may be controlled such that they correspond to a typical concentration of the corresponding lyocell-based special product. This means in the described example, that the bit set of the primary marker bits 192 for ensuring the additional forgery-resistance should preferably not only be "zero" ("zero" means that the bit sequence 182 and the bit set, respectively, is set without any marker bits). The bit set of the secondary marker bits 194 may, in contrast, be an empty bit set, such that the whole possible extent of the binary representation range of the set of secondary markers 194 can be used.

By the possibility of the independent presence of the single primary marker bits 192, it may be ensured that, by the set of primary marker bits 192, all possible combinations in a lyocell-product 150 can be encoded and thus be mapped. The following example illustrates these combinatorial possibilities: when a bit which is defined by the presence of a certain concentration of colorant residues, and a further bit which is defined by the presence of a certain concentration of cotton fibers are regarded, the following four states can be encoded:

| Colorant bit | Cotton bit | Encoding |
|---|---|---|
| 0 | 0 | Uncoded normal lyocell product |
| 1 | 0 | Lyocell product with recyclate which was already colored |
| 0 | 1 | Lyocell product with recyclate made of cotton |
| 1 | 1 | Lyocell product with recyclate made of cotton which was colored |

By the additional secondary marker bits 194, independently from the product composition, different further product details may be encoded. In this way, for example by the following five secondary marker bits 194 (SM0 to SM4), the following additional information can be encoded:

| SM0 | SM1 | SM2 | SM3 | SM4 | Meaning |
|---|---|---|---|---|---|
| 0 | 0 | x | x | x | Manufacturer = v |
| 0 | 1 | x | x | x | Manufacturer = w |
| 1 | 0 | x | x | x | Manufacturer = y |
| 1 | 1 | x | x | x | Manufacturer = z |
| x | x | 0 | 0 | 0 | Year of manufacture not encoded |
| x | x | 0 | 0 | 1 | Year of manufacture 2018 |
| x | x | 0 | 1 | 0 | Year of manufacture 2019 |
| x | x | 1 | 0 | 0 | Year of manufacture 2020 |

A fiber as molded body 102 and a product 150, respectively, with the combination SM0=0, SM1=1, SM2=0, SM3=1, SM4=0 of secondary marker bits 194 may mean in this example: manufactured by the manufacturer "w" in the year 2019.

In combination with the set of primary marker bits 192 according to the above illustration (cotton bit=0, colorant bit=1), together with the set of secondary marker bits 194 SM0=0, SM1=1, SM2=0, SM3=1, SM4=0 may then mean: lyocell fiber manufactured by manufacturer "w" in the year 2019 with a portion of recyclate which has been recovered from dyed fibers.

According to an exemplary embodiment, the secondary markers 194 may in particular consist of a luminescent material (for example as a specialized form of the marking with rare earths). Inorganic luminescent materials may be suitable for performing a test with respect to the originality of a recyclate product directly by a consumer at the location of the sale of the product 150.

Certain substances and components, respectively, may be applied both as primary markers 192 and as secondary markers 194. For example, fluorescent luminescent materials are usable as originality markers. Optical brighteners which constitute a controllable or selectable portion of a recyclate have nevertheless very similar optical and physical, respectively, properties. Thus, depending on a detail-functionalization, a dosing and sub-properties, such a luminescent material, according to an exemplary embodiment of the invention, can be utilized as primary marker 192 or as secondary marker 194.

While the primary markers 192 may constitute independent single bits (i.e. may be orthogonal), the secondary markers 194, depending on the encoding, may form multiple, but for example at least one binary number. Such a binary number may have an individually set meaning and encoding, respectively, which is used only production-internally, for example. On the other hand, this encoding can also be stored at a storing location, in order to ensure the originality of the product 150 in the case of litigation, for example, such that the end customer can perform a testing by himself. The generic representation of the combination of primary marker bits 192 and secondary marker bits 194 to a super bit set is represented in the manner shown in FIG. 2, for example.

According to an exemplary embodiment of the invention, by a mixing in the spinning solution 104 and in the dope, respectively, the marker materials may be kept in a homogenous distribution (and preferably finely dispersed), such that, for the detectability of the primary marker bits 192 and the secondary marker bits 194, a homogenous distribution over large fiber amounts and product amounts, respectively, is generated. In particular, such a homogenous distribution also enables a very low dosing for certain marker materials (for example trace elements, in particular metals, further in particular rare earth metals). In particular for the use of marker materials in nanoscale size, it is advantageous to adjust a high dispersion. For example, this may be achieved or at least supported by applying ultrasound and/or microwaves.

According to an exemplary embodiment of the invention, the described marking principle is used in an industrial scale. By means of the analysis of the primary marker bits 192 in the recyclate, the factor of the textile-substance cycle can be determined. This factor in turn may be used for the control of the recyclate portion and the recyclate composition. Due to degradation and a consequent reduction of the average degree of polymerization, a cellulose fiber 108 may pass the substance cycle of a lyocell-method multiple times (for example six times) without losing its capability for being recycled. The lyocell-molded body 102 which is encoded via the primary and secondary marker bits 192, 194, allows for the performance of the corresponding measurement methods and control methods for an estimation of the textile-substance cycles and the control of the recyclate quality of a recyclate which is added to the lyocell-production.

In another exemplary embodiment of the invention, one or more contrast agents or indication agents are added to the dope and the spinning solution 104, respectively, which may be detected in the resulting cellulose fiber 108. The different additives may in turn be involved in the encoding as single bits of the super bit set. The contrast agents and indication agents which are utilized according to the described embodiment, may be determined by different detection methods. These include magnetic resonance imaging (NMR-spectroscopy), microscopic methods, in particular fluorescence measuring methods, x-ray methods, infrared spectroscopy and Raman-spectroscopy, and photoelectron spectroscopy (PES), in particular x-ray-PES and ultraviolet-PES (XPS and UPS, respectively). Also methods for measuring a molecular weight distribution and/or extractable ingredients of the product 150 or the molded body 102 may be used in this respect. The same applies for methods for detecting colorant residues in the product 150 or its preform. Contrast agents or identification agents may be utilized as secondary marker bits 194 due to their independence. Other contrast agents or identification agents may contribute to a function or a result in the cellulose fiber 108 and may thus be utilized as primary marker bits 192 with advantage. These materials are preferably used in nanoscale and in low concentrations. With advantage, one or more of the following materials may be utilized:

| Material group | Primary/secondary marker bits |
|---|---|
| Particles with fluorescent and/or phosphorescent properties | Primary and secondary |
| Combined, multimodal systems for signaling | Secondary |
| Pigments made of recyclates | Primary |
| Magnetic contrast agent | Primary |
| X-ray contrast agent | Secondary |
| Inorganic microparticles and/or nanoparticles Shape-selected particles | Secondary |

In a preferred embodiment, at least two primary markers are used which are assigned to at least two primary marker bits 192. By the measurement of the proportion of the marker amounts with respect to each other, conclusions with respect to the dilution in the substance cycle and enrichments, respectively, of foreign matters can be drawn during the input inspection of the recyclate, prior to the lyocell-process.

In a further preferred embodiment, small amounts of a luminescent material marker are added. In order to achieve that these are less chemically attacked by the lyocell-process or the viscose-process, prior to adding them into the dope and the spinning solution 104, respectively, they may be surrounded by a (for example nanoscale glass-type) enclosure (for example by a Sol-Gel-process). By embedding directly into the dope and into the spinning solution 104, respectively, a high washing-protection and thus a high forgery-protection in the product may be achieved. With a suitable dosing of this secondary marker, for a direct identification of the recyclate product by the customer, by means of a stationary spectroscopic analyzer, the authenticity of the use of the recyclate can be directly determined by the customer itself. An optional additional variant consists in realizing an app on a mobile device (for example a mobile phone, such as a smart phone) which is capable of performing the required spectroscopic evaluations. In this way, the customer itself, without support, may test the authenticity of products 150, for which a recyclate portion or a closed substance cycle is claimed.

A lyocell-molded body 102 which is manufactured according to the lyocell-method, according to an exemplary embodiment of the invention, may comprise a recyclate portion (in particular a portion of old clothes in the starting material 110) of at least 3 weight percent, and may comprise at least one intrinsic constituent for the use as marker with the following marker criteria:

a) a portion of rare earth elements of at least 1 ppm, in particular of at least 5 ppm b) a portion of $TiO_2$ of at least 5 ppm, in particular of at least 10 ppm c) a portion of residual constituents of colorants of at least 10 ppm, in particular of at least 20 ppm d) a portion of metal oxides of preferably at least 50 ppm e) a portion of a shape-selected particle (for example a spherical particle) of at least 1 particle per $mm^3$ molded body volume, preferably more than 10 particles per $mm^3$ molded body volume.

With advantage, the lyocell-molded body 102 may contain a luminescent material, preferably an inorganic luminescent material.

The lyocell-molded body 102 and the product 150, respectively, may be tested by means of a spectroscopic method with respect to primary markers and/or secondary markers. This spectroscopic method may be applied in the context of a sales process of the product 150, for example. This may be performed for single markers or for all markers.

Thus, the lyocell-molded body 102 and the product 150, respectively, may be tested by means of a preferably mobile device with respect to primary markers and/or secondary markers. This may be performed for single markers or for all markers.

Figure 3:
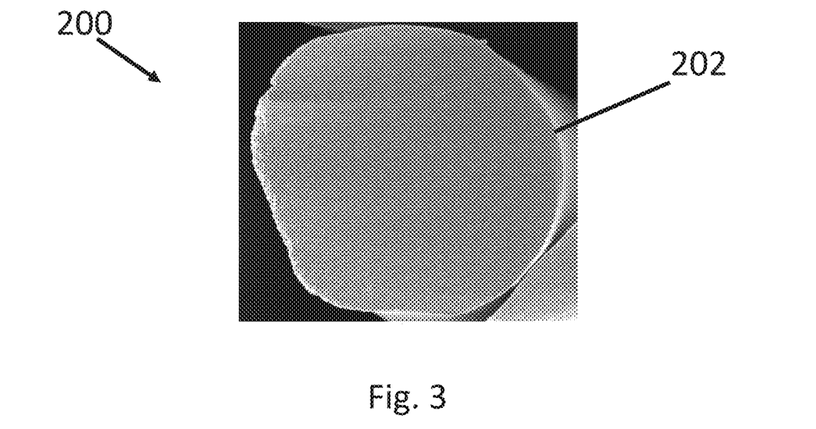
FIG. 3 shows a cellulose fiber manufactured by a lyocell-method.

FIG. 3 shows a cellulose fiber 200 which is manufactured by means of a lyocell-method in cross-section. The cellulose fiber 200 which is manufactured by means of a lyocell-method has a smooth round outer surface 202 and is homogenous and free from macroscopic holes, filled with cellulose material. Therefore, it can be unambiguously distinguished from cellulose fibers which are manufactured by means of a viscose-method (see reference sign 204 in FIG. 4) and from cellulose fibers of cotton plants (see reference sign 206 in FIG. 5) by a person skilled in the art.

Figure 4:
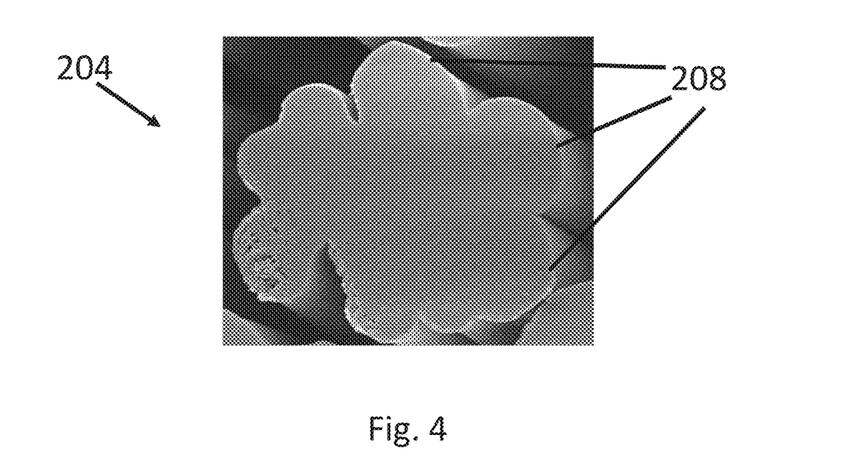
FIG. 4 shows a cellulose fiber manufactured by a viscose-method.

FIG. 4 shows a cellulose fiber 204 which is manufactured by means of a viscose-method in cross-section. The cellulose fiber 204 is cloud-shaped and comprises a plurality of arc-shaped structures 208 along its outer circumference.

Figure 5:
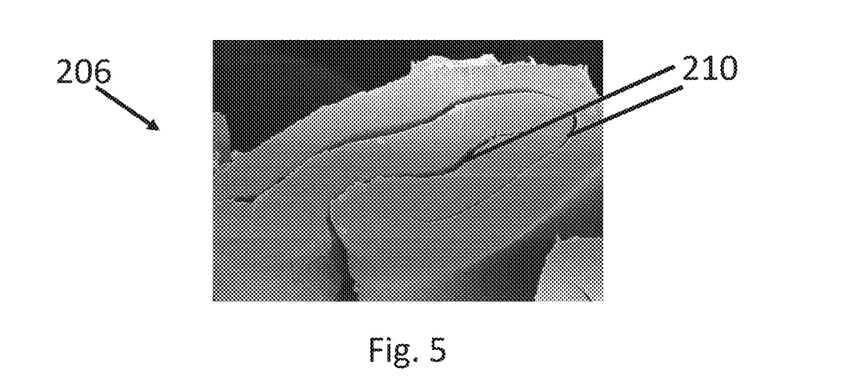
FIG. 5 shows a natural cellulose fiber of a cotton plant.

FIG. 5 shows a natural cellulose fiber 206 of a cotton plant in cross-section. The cellulose fiber 206 is kidney-shaped and comprises a lumen 210 which is free from material as a fully circumferentially enclosed hollow in an interior.

By means of the significant geometric and structural, respectively, differences of the fibers according to FIG. 3 to FIG. 5, it is possible for a person skilled in the art to unambiguously determine, for example by means of a microscope, if a cellulose fiber is formed by means of the lyocell-method, by means of the viscose-method, or naturally in a cotton plant.

By means of the phenomena described with respect to FIG. 3 to FIG. 5, also a shape (for example determined by a microscope) of the cellulose fibers 108 in a product 150 and a preform of the same (for example a molded body 102), respectively, may be used to identify a test product 158.

In addition, it should be noted that "comprising" does not exclude other elements or steps and "a" or "an" does not exclude a multiplicity. Furthermore, it should be noted that features or steps which are described with reference to one of the above embodiments may also be used in combination with other features or steps of other above described embodiments. Reference signs in the claims should not be construed as a limitation.

The invention claimed is:

1. Method, performed by one or more processors, for identifying a product which comprises cellulose by encoding information about a composition of multiple constituents of the product or of a preform of the product, the method comprising:

storing a plurality of composition data structures indicative of multiple constituents of a plurality of products or preforms of the plurality of products respectively in a database, stored in a storage device;

wherein the multiple constituents include intrinsic non-cellulosic constituents of the products or the preforms, and wherein the stored composition data structures include intrinsic non-cellulosic constituents of each of the products or the preforms originated from old textiles which have been used as a starting material to produce the products or the preforms;

measuring a composition of constituents of a product under test or a preform of the product under test, by a measuring device controlled by the one or more processors;

encoding the measured composition in a measurement data structure, as a fingerprint of the product under test or its preform;

comparing the fingerprint with the stored composition data structures, by the one or more processors; and when there is a match between the footprint and a stored composition data structure, identifying the product under test or its preform as a product comprising cellulose, and determining whether the product under test has been manufactured based on a recycled cellulose source as a part of the starting material.

2. Method according to claim 1, wherein the product under test or its preform is manufactured on basis of old clothes as cellulose source as at least a part of the starting material.

3. Method according to claim 2, wherein the product under test or its preform is partially manufactured on basis of at least one material of a group which is consisting of wood pulp, rags pulp, cotton, cellulose manufactured by a lyocell-method, and cellulose manufactured by a viscose-method.

4. Method according to claim 1,
wherein the product under test or its preform is manufactured on basis of the starting material which is manufactured as inhomogeneous mixture of different constituents; or
wherein the product under test or its preform is manufactured by the lyocell-method or by the viscose-method.

5. Method according to claim 1, further comprising:
determining at least one other data structure which is indicative for multiple constituents of at least one other product or a preform of the at least one other product;
correlating the least one other data structure with the at least one other product or its preform; and
storing the least one other data structure in the database.

6. Method according to claim 1, further comprising:
identifying the test product under test or its preform as the product comprising cellulose when:
a highest number of accordant bit criteria with respect to a bit sequence in the footprint which is indicative for a composition of the product under test or its preform includes the at least two constituents; and
a discrepancy between the footprint and the stored composition data structure and does not exceed a predetermined threshold value.

7. Method according to claim 1,
wherein the plurality of composition data structures is indicative for a combination of constituents which are present in the products, and their respective amount;
wherein the multiple constituents relate to non-cellulosic constituents of the product under test or its preform; and
wherein at least one of the multiple constituents relates to at least one cellulosic constituent of the product under test or its preform.

8. Method according to claim 1, further comprising storing a bit sequence in the database which is indicative of a composition of the product under test or its preform made of at least two constituents.

9. Method according to claim 8, wherein the bit sequence comprises:
at least one primary marker bit with contextual or functional or material with respect to lyocell-based product or lyocell-based preform; and wherein
at least one secondary marker bit concerning materials of the lyocell-based product or the lyocell-based preform with a pure marker character, without contextual or without functional or without material with respect to lyocell-based product or lyocell-based preform.

10. Method according to claim 1, wherein the product under test or its preform comprises molded bodies.

11. Method according to claim 10, wherein the molded bodies are regenerated cellulosic molded bodies fibers, foils, sponges, or spheres.

12. Method according to claim 1, wherein the multiple constituents relate to intrinsic constituents of the product under test or its preform which have been already contained in and/or at the molded bodies after an extrusion of a spinning solution to cellulosic molded bodies.

13. Method according to claim 7,
wherein the intrinsic non-cellulosic constituents comprise at least one of a group which is consisting of a trace element, in particular a metal, further in particular a rare earth metal, a metal oxide, in particular titanium dioxide and/or zinc oxide, a colorant, a luminescent material, and a synthetic plastic, in particular elastane and/or polyester.

14. Method according to claim 1, wherein the information which is measured and stored in the database is used as a code for identifying an origin of the cellulose product or a preform of the product.

15. Method according to claim 1, wherein the product under test or its preform is manufactured on basis of remains of a clothing manufacture as cellulose source as at least a part of the starting material.

* * * * *